United States Patent [19]

Zacharias

[11] Patent Number: 4,763,513
[45] Date of Patent: Aug. 16, 1988

[54] SONIC TRANSDUCER

[75] Inventor: Ellis M. Zacharias, Tulsa, Okla.

[73] Assignee: Nusonics, Inc., Tulsa, Okla.

[21] Appl. No.: 947,434

[22] Filed: Dec. 29, 1986

Related U.S. Application Data

[63] Continuation-in-part of Ser. No. 702,349, Feb. 15, 1985, Pat. No. 4,649,754, which is a continuation-in-part of Ser. No. 464,416, Feb. 7, 1983, Pat. No. 4,505,160.

[51] Int. Cl.$^4$ .................... G01N 29/02; H04R 17/10
[52] U.S. Cl. .................................. 73/61 R; 73/644; 310/327; 310/335
[58] Field of Search .................... 73/861.18, 597, 632, 73/644, 61 R; 310/327, 334, 335, 336; 367/162, 163, 165

[56] References Cited

U.S. PATENT DOCUMENTS

| | | | |
|---|---|---|---|
| 3,890,423 | 6/1975 | Zacharias, Jr. | 310/335 |
| 3,935,484 | 1/1976 | Leschek et al. | 310/327 |
| 4,240,004 | 12/1980 | Coleman | 310/327 |
| 4,287,755 | 9/1981 | Mansfield | 73/61 R |
| 4,417,480 | 11/1983 | Zacharias, Jr. | 73/861.18 |

Primary Examiner—Charles A. Ruehl
Attorney, Agent, or Firm—Head & Johnson

[57] ABSTRACT

An improved transducer for transmitting and receiving sonic energy, the transducer having a housing with a cylindrical opening, an acoustic end member closing one end of the opening, and providing an acoustic window, a crystal element having one planar surface in engagement with the acoustic end member rearward face, a thrust producing compression screw threadably received in the cylindrical opening, and a spring between the compression screw and crystal element to maintain a substantially steady force of the crystal element against the acoustic end member rearward face. In one embodiment particularly adapting the transducer for sanitary environments the end member includes an integrally formed reflector portion with provision for fluid to flow freely between the sonic window portion and the reflector portion.

25 Claims, 4 Drawing Sheets

SONIC TRANSDUCER

CROSS-REFERENCE OF THE INVENTION

This is a continuation-in-part of U.S. patent application Ser. No. 702,349 filed Feb. 15, 1985 and entitled "High Pressure Transducer", now U.S. Pat. No. 4,649,754, which, in turn, is a continuation-in-part of U.S. patent application Ser. No. 464,416 filed Feb. 7, 1983 and entitled "High-Temperature Transducer", now U.S. Pat. No. 4,505,160.

SUMMARY OF THE INVENTION

The use of sonic transducers in industry is well known, such as in flow meters. A particular application of the use of sonic energy to which the present invention is directed is to monitor the properties of a fluid medium. The present invention is particularly adaptable for providing indications of the characteristic of liquid products in a sanitary environment. For this purpose the transducer must be positioned so that the sonic energy emanating from the transducer is coupled directly to the liquid medium. Transducers may be used singly wherein a reflective surface is provided so that the same transducer both transmits and receives sonic energy, or transducers may be arranged in pairs so that they talk to each other through the liquid medium. The present disclosure includes an improved transducer having a self-contained reflective surface.

By transmitting and receiving sonic energy in a liquid material, the characteristics of the material can be measured and departures from established norms can be expeditiously detected. The velocity of sound travel in a liquid material is an indicator of the characteristics of the material, such as the specific gravity and amount of dissolved solids. In addition, by measurement of sound energy loss, that is, attenuation caused by absorption or scattering, other characteristics of the liquid material can be monitored.

One difficulty in using transducers in this application is that they may be exposed to high temperature fluctuations. A second problem with the application of transducers for this purpose is that they must be sealed effectively to prevent entrance of fluid into the transducer, yet in a manner which does not employ elastomers or other type of gasket arrangements which would be destroyed by high temperatures or by chemical attack to which the transducers are subjected.

In addition, many applications of transducers used for monitoring food products such as jelly, milk and the like must be constructed to meet rigid sanitary requirements. This means the portion of the transducer exposed to food products must be free of crevices and recesses which can collect food particles that might promote bacteria growth. In addition, in some applications it is important that the transducer be designed to be self cleaning, that is, so that it can be cleaned by circulating cleaning liquid or steam past the transducer without requiring the transducer to be removed for cleaning.

The transducer of this invention includes a housing having a cylindrical opening in it. Closing one end of the opening is a metallic acoustic end member providing an acoustic window. In the preferred embodiment this end member is welded into place, thereby preventing leakage of fluid or gases into the interior of the transducer. The acoustic end member has a rearward surface in alignment with the tubular opening. In contact with this rearward surface is a cylindrical crystal, such as a piezoelectric element having a forward face and rearward face. In order to achieve efficiency in the transmission of sonic energy from the crystal element to the acoustic window, the faces of these two elements must be in secure, intimate contact. Any deviation which causes gaps or low pressure areas of contact between the crystal element and the acoustic window will impair the effectiveness and efficiency of the transducer.

Rearwardly of the crystal element within the cylindrical opening is a dampening means which preferably is in the form of a plurality of cylindrical washers made of non-ferrous metal such as copper, brass, or the like. Rearwardly of the absorption member are elements whose function is to apply pressure against the absorption member and thereby the crystal to ensure intimate contact between the crystal and the acoustic window. In the present invention these elements include a first cylindrical thrust imparting disc which engages the absorption member and a second thrust imparting disc. Each of the thrust imparting discs has a small depth recess in one end surface coincident with the cylindrical axis. A thrust imparting sphere is positioned between the discs and in the recesses. A means is provided of applying force against the rearward-most thrust imparting disc. In the preferred arrangement the rearward portion of the cylindrical opening is internally threaded and an externally threaded compression screw is received in the threaded opening. The inner end of the screw engages the thrust discs by way of electrical contact washers as the member is threadably advanced, forcing the crystal element into contact with the acoustic window rearward face. The thrust/transmitting sphere allows application of force so that defects arising from machining tolerances in the device are compensated for, and thereby the thrust is equally applied to the full rearward face of the crystal element to achieve maximum effective force distribution of the crystal element forward face against the acoustic window rearward face.

An important aspect of the present invention is provision of means to maintain good physical contact between the crystal element and the sonic window over varying temperature conditions. For this purpose a spring is positioned between the compression screw and the thrust discs. In this manner, as the thrust imparting portions of the assembly expands or contracts with temperature change, the spring compensates, maintaining a secure force of the crystal element with the sonic window. The spring may be in the form of a plurality of Belleville washers or a helical spring.

Another important aspect of the present invention is that it provides a transducer particularly adaptable for sanitary applications. Transducers are frequently utilized in the food industry to monitor liquid food products such as jelly, jam, milk, etc. By measuring the speed of sound characteristics of food products various parameters can be determined. For instance, in measuring the speed of sound transmission of milk the butterfat content can be accurately ascertained. When measuring the speed of sound transmission in jelly or jams, the specific gravity is indicated which in turn is indicative of the sugar content of the products. Various other applications of sonic measurements in connection with the manufacture of food products are known and sonic instrumentation has been used in food product processing to improve the control of the quality and consistency of the products.

One problem with the use of sonic instrumentation with food products is that sanitary stringent conditions must be maintained. In addition, it is highly desirable that the transducer be configured such as to be susceptible of cleaning in place. This means that the transducer is preferably cleaned by flowing a cleaning fluid past the transducer to clean it without requiring that the transducer be removed for cleaning. For these purposes the present invention provides a transducer having a cylindrical housing and having an acoustic end member which sealably closes the forward end of the housing. The housing has a cylindrical opening through it which receives the transducer crystal element and the means for applying force to the transducer element as previously discussed. The acoustic end member is formed of two basic portions, the first being a rearward portion which forms the sonic window of the transducer; the second being a forward portion providing a reflective or target surface. These portions are integrally supported relative to each other by spaced apart leg portions. The entire acoustic end member is formed of a single piece of metal with smooth contoured surfaces free of crevices. The acoustic end member is welded to the cylindrical transducer body and after welding the transducer body and end member are turned and polished to eliminate any spacing or crevices. In this way, a transducer having an integral target reflective surface is provided and the entire assembly is free of crevices. By the smooth contoured configuration the transducer and integral target are susceptible of being cleaned in place by passing cleaning fluid past the transducer.

For additional background information and for examples of sonic transducers of the type to which the present invention applies, reference may be had to the following U.S. Pat. Nos.: 3,771,117; 3,890,423; 3,935,484; 3,973,152; 4,162,111; 4,240,004; 4,331,025; 4,365,518; and U.S. Pat. No. Re. 29,785.

DESCRIPTION OF THE DRAWINGS

FIG. 6 is a cross-sectional view which is a variation of the design of FIG. 5. In this instance, the length of the transducer has been increased and an internal spacer of appropriate length has been used to take up the additional space between the compression screw in the top of the transducer and the helical spring. This figure also shows a variation in the type of flange which may be used.

FIG. 7 is still another embodiment of the transducer of this invention which employs a pipe thread on the upper end so that the transducer may be threaded into a mounting surface. A seal is accomplished by virtue of the engagement of the pipe threads of the transducer with the mating pipe threads of the mounting surface.

FIG. 8 is a cross-sectional view taken along the line 8—8 of FIG. 6 showing the legs which support the integral reflective portion to the transducer.

FIG. 9 is an end view of the transducer of FIG. 7 showing the appearance of the end of reflecting portion of the transducer.

DESCRIPTION OF THE PREFERRED EMBODIMENT

Figure 1:
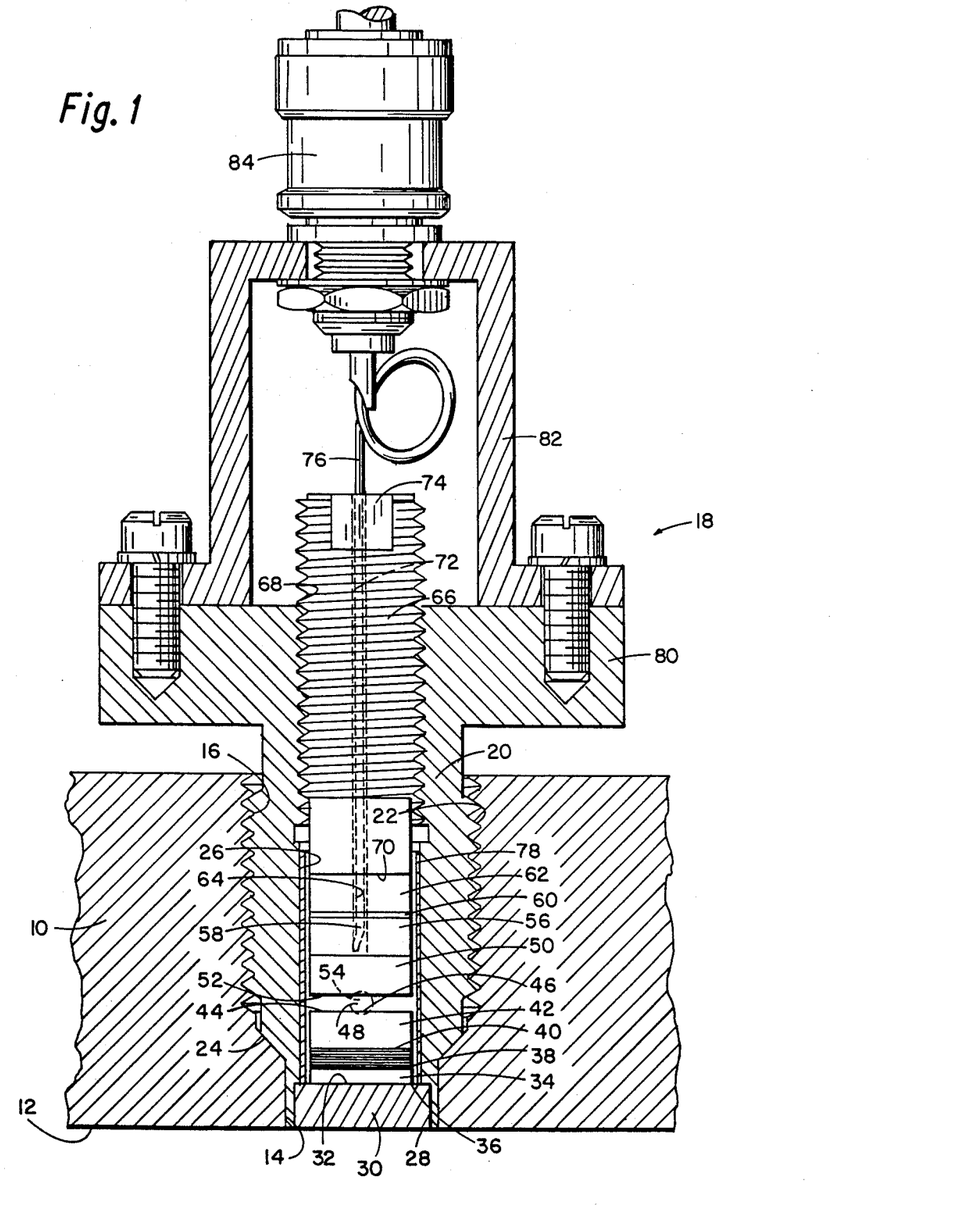
FIG. 1 is a cross-sectional view of one embodiment of the invention in which the transducer housing is received in an internally threaded opening formed in a device. The transducer housing is provided with a removable bonnet for the attachment of an electrical connector to the transducer.

Referring now to the drawings and first to FIG. 1, an embodiment of the invention is illustrated. The invention, as has been previously mentioned, may be employed such as in monitoring fluid as it flows through a passageway, and in such application, the passageway housing is indicated by the numeral 10 with the flow passageway for the fluid indicated by the numeral 12. The housing 10 has an opening 14 which communicates with the flow passageway 12, the outward portion of the opening 14 being of enlarged internal diameter and threaded at 16. The transducer is generally indicated by the numeral 18 which includes a cylindrical body 20 having external threads 22. The exterior configuration of the transducer body 20 is configured to sealably engage the opening 14 in housing 10, including the provision of an internal shoulder 24.

The body 20 has a cylindrical opening 26 which receives the elements making up the operative part of the transducer. The inward end of cylindrical opening 26 is of enlarged diameter at 28 and receives an acoustic window element 30. The element 30 is formed of material which is highly conductive of sonic energy, such as of metal. In addition, the acoustic window 30 must withstand the high temperatures and high pressures to which the housing 10 is subjected. The acoustic window 30 is preferably welded in position in opening 28 to thereby form a sealed closure of the lower end of the interior of cylindrical opening 26.

The acoustic window 30 has a planar rearward surface 32. Positioned in contact with this surface is a cylindrical transducer crystal element 34 having a forward planar surface 36 and a rearward planar surface 38. It is extremely important that the crystal element forward surface 36 have initimate contact with the acoustic window rearward surface 32 in order to achieve efficient acoustic coupling of these two elements. The pressure of contact of these surfaces must not only be such as to eliminate the possibility of voids but the pressure needs to be evenly distributed over the entire surface areas. An important aspect of this invention is the provision of means to achieve such equal pressure distribution.

The next element in the assembly is a cylindrical dampening member 40. While the dampening members of a variety of materials and configurations have been employed in transducers, an effective dampening means is the use of a plurality of thin discs of metal such as brass or copper. In a typical embodiment, the dampening member 40 may be made up of approximately 20 thin metal discs.

Rearwardly of the dampening member is a first thrust disc 42 which has, on its rearward surface 44, a small diameter recess 46, the recess being coincident with the cylindrical axis of the disc. The disc is formed of an electrically conductive material having good high temperature strength such as INCONEL 625. "INCONEL" being a trademark of International Nickel Company.

Next is a thrust transmitting sphere 48 which is formed of very hard electrically conductive material, such as tungsten carbide. A second thrust disc 50 is of the same configuration as first thrust disc 42, that is, in its forward face 52 there is a small diameter recess 54 coincident with the disc cylindrical axis, the recess 54 receiving the thrust transmitting sphere 48.

Rearwardly of the second thrust disc 50 is an electrical contact washer 56 having an axial opening 58 therethrough. In contact with the rearward surface of the electrical contact washer 56 is an insulator 60 which may be formed of material such as mica or other material which can withstand the temperature to which the transducer is subjected.

Contacting insulator 60 is a second washer 62 having an axial opening 64 therethrough. Rearwardly of the washer 62 is an externally threaded compression screw member 66. This member is received in the upper internally threaded portion 68 of the cylindrical opening 26 in transducer body 20. The lower end face 70 of the compression screw engages washer 62, the end face being perpendicular the longitudinal axis of the compression screw. An axial opening 72 extends through the compression screw. A wrench flat 74 is formed on the exterior outer end to afford means of rotation of the screw. Received in the axial openings provided in elements 56, 60, 62, and 66 is an insulated conductor 76. The bare or exposed end of the insulated conductor is attached to the electrical contact washer 56. Received within the cylindrical opening 26 in the transducer body is a tubular insulating member 78. Conductor 76 thereby provides an electrical path to the rearward surface 38 of the crystal element 34.

Formed integrally as a part of the outer end of the body 20 is a flange portion 80 which receives a cylindrical bonnet member 82. An electrical connector 84 is attached to the bonnet portion and provides means for connecting a cable having continuity with the insulated conductor 76. The purpose of the bonnet portion 82 is to afford means of attaching an electrical connector at sufficient spacing so as to reduce the possibility of overheating of the electrical connector 84.

As previously indicated, it is extremely important that the pressure contact of the crystal element 34 with the acoustic window 30 be maintained at all temperatures to which the transducer is subjected. This is accomplished by inwardly threading the compression screw 66. The force applied by the compression screw is transmitted through the washer 62, insulator 60, electrical contact washer 56, second thrust disc 50, thrust transmitting sphere 48, first thrust disc 42, and dampening member 40 to the crystal element 34. Any misalignment or machining tolerances in manufacturing the various elements making up the transducer are compensated for by the thrust transmitting sphere 48. In this manner the pressure applied against the crystal member rearward surface 38 is transmitted evenly over the entire area of the crystal forward surface 36 acoustic window rearward surface 32. It should be also noted that the force is transmitted throughout in a linear path and with only a single force adjustment which is accomplished by the rotation of compression screw 66.

Figure 4:
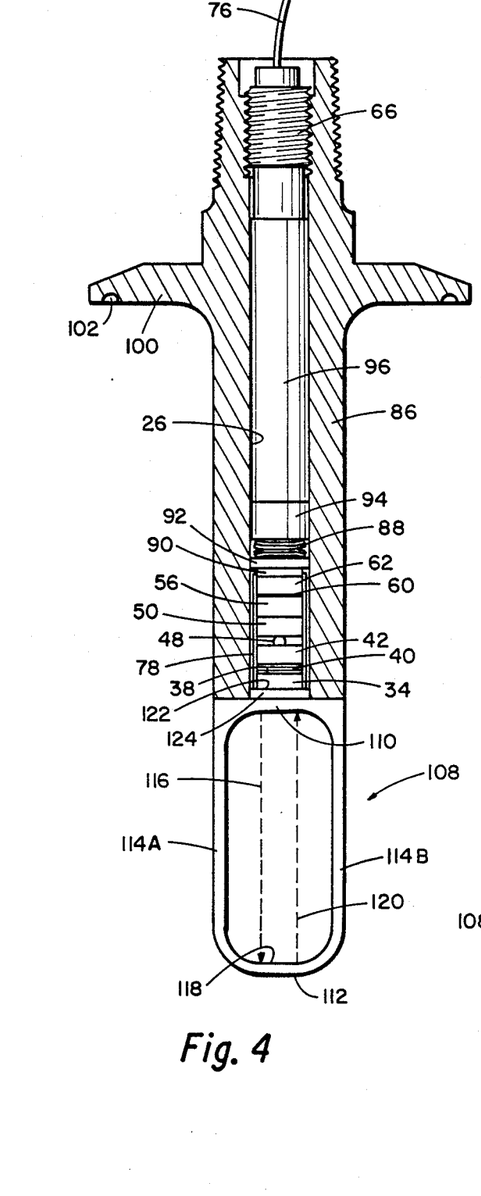
FIG. 4 is a cross-sectional view of the clean-in-place transducer of FIG. 3 and showing the arrangement of internal components. A feature of the transducer as shown in FIGS. 2, 3 and 4 is the integral sanitary flange which contains a groove for a sealing gasket or O-ring.

In FIG. 4 a transducer body 86 which is comparable to the body 20 of FIG. 1 forms the basic structure of the transducer. The basic elements of the thrust parting means of FIG. 1 are utilized to ensure a firm contact of the transducer crystal element 34 with the sonic window; however, FIG. 4 shows a significant contribution to the arrangement of FIG. 1 in the provision of a spring 88 in series with the thrust parting elements. Specifically, spring 88 is positioned between the compression screw 66 and the transducer crystal 34. A third washer 90 is in contact with second washer 62. Above it is a fourth washer 92. Washers 62, 90 and 92 may be formed as one piece if desired. Spring 88 is in contact with the upper surface of fourth washer 92. Above spring 88 is a fifth washer 94. Between the compression screw 66 and fifth washer 94 is a tubular spacer 96. Elements 94 and 96 may be combined into one unit.

Figure 5:
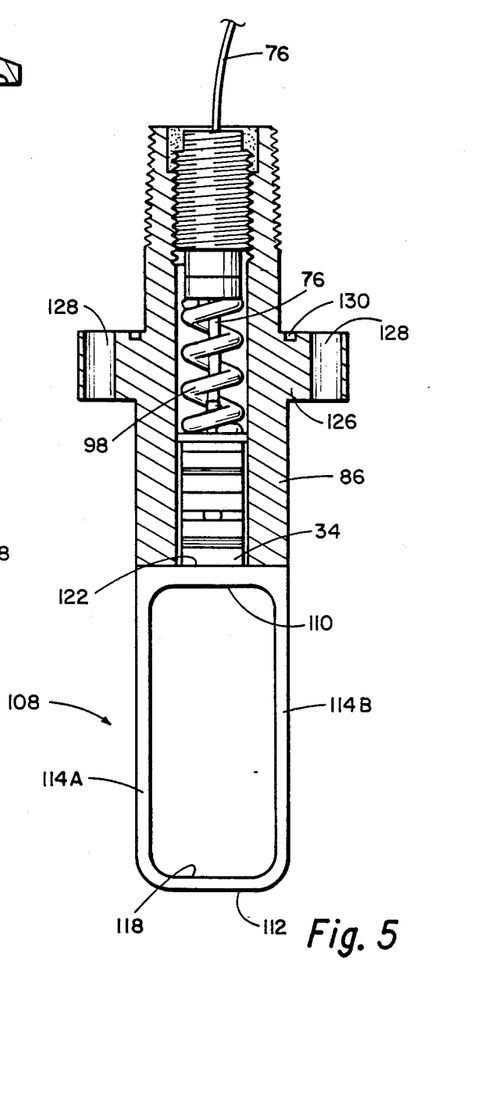
FIG. 5 is another embodiment of the transducer which is suited for general purpose process monitoring where clean-in-place and sanitary requirements do not apply. A flange is formed as part of the body, either integrally or welded to it, and is used for attachment to a mounting surface by means of plurality of screws.

In the arrangement illustrated in FIG. 4 the spring 88 is in the form of a plurality of Belleville washers which are cupped shaped washers. When these cup-shaped spring washers are subject to compression they resist flatening and thereby exert a resilient biasing force. FIG. 5 has an internal arrangement comparable to that of FIG. 4 except that the spring in FIG. 5 is in the form of a helical spring 98.

The use of a spring, either in the form of Belleville washers 88 or helical spring 98 serves to maintain constant pressure of the crystal element 34 against the sonic window. As the transducer is subject to temperature fluctuations the spring adjusts, maintaining a substantially continuous pressure of the crystal element against the sonic window rearward face whereas, without such resilient biasing force the application of pressure against the crystal element can vary considerably. In some instances, if the temperature to which the transducer is subjected falls to a low level, pressure on the crystal element can decrease to a point where the transmission of sonic energy from the crystal element to the sonic window is impaired. On the other hand, under extreme high temperatures, the force applied may be excessive, causing damage to the crystal element. By the use of a spring both excesses are alleviated.

The elements 66, 96, 94, 88, 92, 90, 62, 60 and 56 all have central openings therethrough, as suggested in FIG. 1, whereby the conductor element of a cable 76 can be used to apply voltage to the rearward face 38 of the crystal element 34 in the same manner as has been described with reference to FIG. 1.

Figure 2:
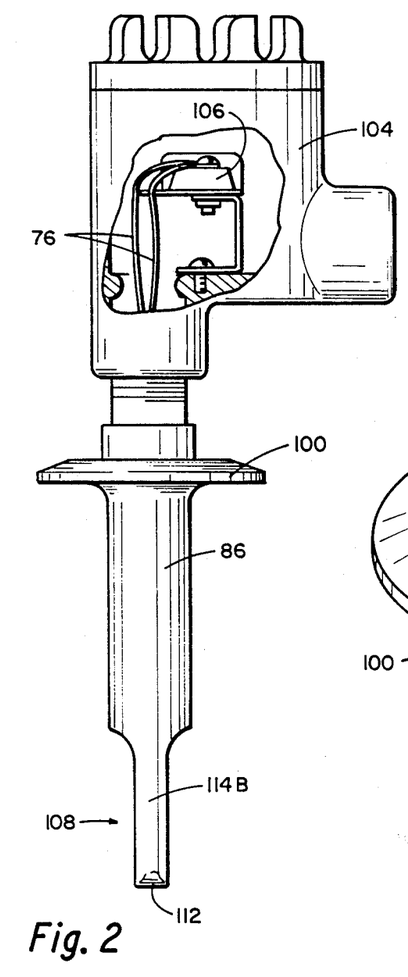
FIG. 2 is an elevational view of a clean-in-place transducer with an electrical connection head attached. A partial sectional view of the connection head reveals the manner in which conductors from the transducer are attached to an electrical terminal strip.
Figure 3:
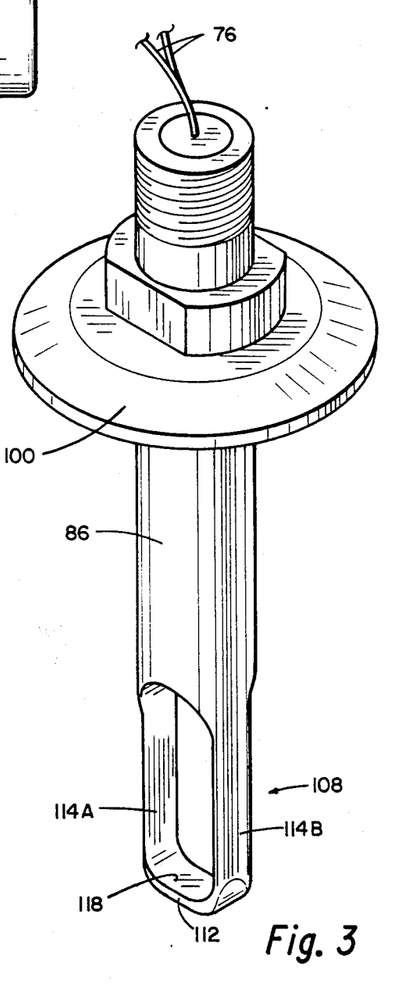
FIG. 3 is an isometric view of the clean-in-place transducer of FIG. 2 with the electrical connection head removed.

The embodiment of the transducer of FIG. 4 is shown in external view in FIGS. 2 and 3. The transducer body 86 in the arrangement of FIGS. 2, 3 and 4 has an integral flange 100 with an O-ring groove 102 therein. This type of groove is particularly adaptable to the mounting of the flange in sanitary services as used in the food and drug industry. FIG. 2 shows a connection head 104 attached to the upper end of the transducer body 86. The head is shown broken away to reveal a connection block 106 by which conductor 76 is attached for connection to a cable (not shown) extending into the connection head.

Of importance to the present invention is the provision of an improved sonic window for the transducer. For this purpose an acoustic end member generally indicated by the numeral 108 is employed, as shown in FIGS. 2 through 8. The acoustic end member has a base portion 110 which seals and closes the cylindrical opening 26 formed in body 86. The acoustic end portion 108 is further defined by a target portion 112 and the portions 110 and 112 are integrally interconnected by leg portions 114A and 114B. The base portion 110 provides the sonic window through which sonic energy is transmitted as generated by the crystal element 34. The sonic energy which passes through the acoustic member base portion 110 is indicated by arrow 116 in FIG. 4. The sonic energy encounters a reflective surface 118 provided by the target portion 112. The reflective sonic energy indicated by the arrow 120 returns through the sonic window portion of base portion 110 to engage crystal element 34. Thus, the acoustic end member 108 serves the triple function of (a) closing the end of the cylindrical opening 26 in body 86; (b) providing a sonic window through which sonic energy is transmitted and received; and (c) providing a reflective target surface at a preselected and accurately maintained distance from the crystal element.

The acoustic end member 108 is preferably welded to the end of body 86 and after welding the entire assembly is turned and polished to provide an exterior surface which is free of voids and crevices into which food particles might lodge and thereby be subject to bacteria action. As shown in FIGS. 2 and 3, the external surface is such as to appear as if the body 86 and acoustic end member 108 were formed of one solid element. Such could be accomplished except that it is important that the interface 122 of the acoustic window formed by the base portion 110 be flat within a high degree of tolerance to receive the equally flat surface of the transducer crystal element 34. In the embodiment shown in FIG. 4 the acoustic end member 108 has an integrally formed circular cross-section raised portion 124 which is received within the cylindrical opening 26. In the arrangement of FIG. 5 the acoustic end member 108 does not have such integral raised portion but has a flat surface across the upper end thereof providing the interface 122 of the crystal elements 34.

The provision of the acoustic end member 108 which is welded to and thereby becomes integral with the body 86 makes it possible to machine a transducer which meets the sanitary requirements of an apparatus for use in the food and drug industry. Since there are no cracks, crevices or joints in which food components may lodge and bacteria develop the overall device is susceptible to being cleaned in place. This means that when the transducer of the type shown in FIGS. 2, 3 and 4 is used in food handling equipment the transducer can be cleaned by passing cleaning fluid through the conduit in which the transducer extends to thoroughly wash the transducer without the requirement that it be removed from its supporting apparatus. This is particularly true of the type shown in FIGS. 2-4 which includes the sanitary flange 100.

A slightly alternate embodiment of the invention as shown in FIG. 5 has a flange 126 having a plurality of bolt openings 128. The flange is either integrally formed with the body 86 as shown or it can be welded in place. O-ring groove 130 is shown on one face of the flange where an O-ring is seated to provide sealing against a mating surface. The internal components of the embodiment of FIG. 5 is the same as that for FIG. 4 except that instead of Belleville washers, a helical spring 98 is employed. The embodiment of FIG. 5 is exemplary of the fact that various flange arrangements may be employed for mounting the improved transducer of this invention.

Figures 6, 7, 8, 9:
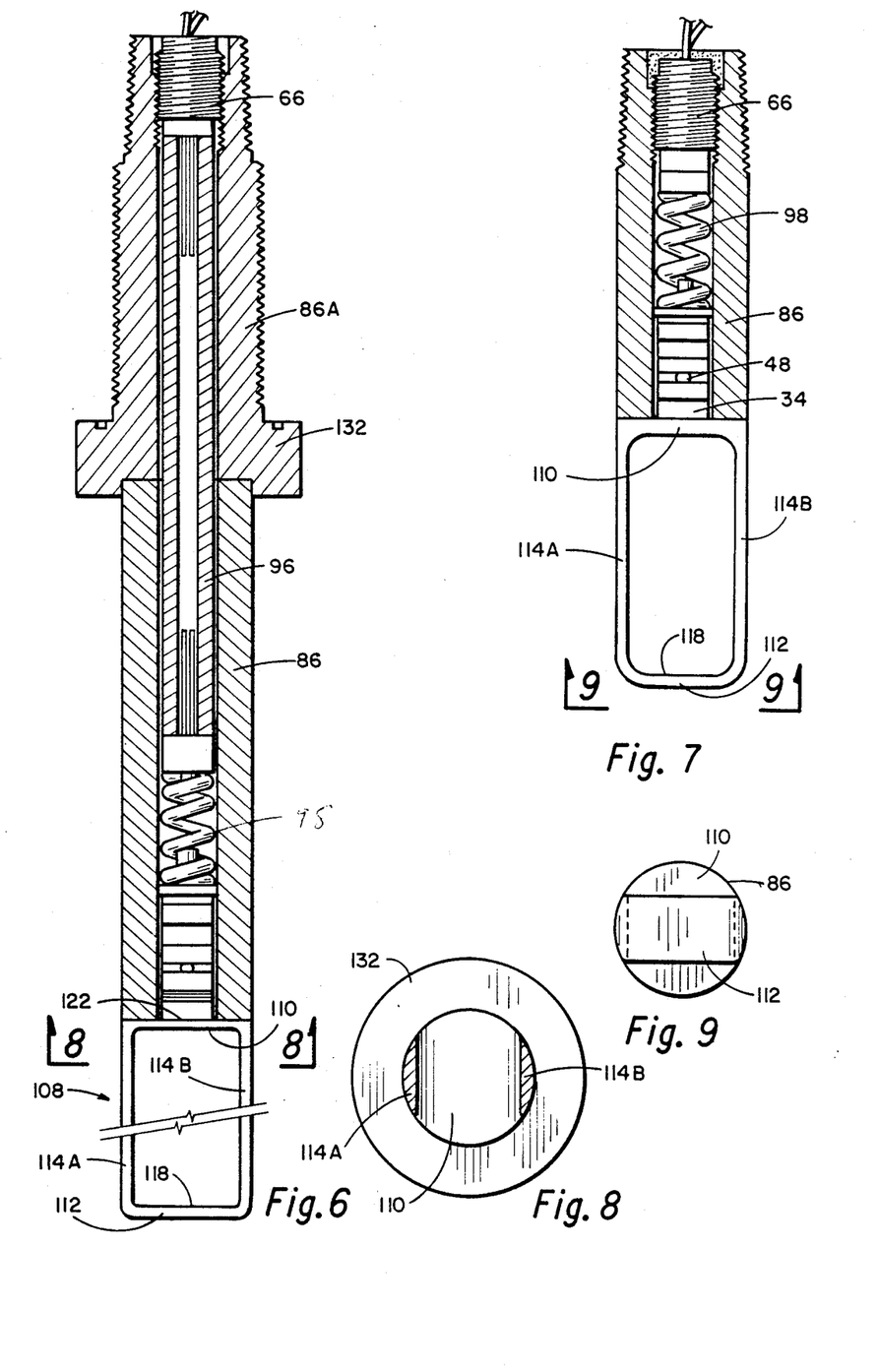

FIG. 6 is an additional alternate embodiment. In this embodiment the length of the transducer body portion 86 has been lengthened and the internal spacer 96 is correspondingly lengthened. In the embodiment of FIG. 6 the upper end of the transducer body is formed of a separate piece 86A and is secured to the main body portion 86 such as by welding. A type of flange 132 is formed with the upper body portion 86A. The flange 132 of the FIG. 6 embodiment is designed to be held against a mating surface by means of a locking nut (not shown). The locking nut may be secured on the external threads formed on body portion 86A. The internal arrangement of the transducer, including the use a of helical spring, is the same as in FIG. 5. In addition the acoustic end member 108 is the same as that described with reference to FIG. 5.

FIG. 7 shows an additional alternate embodiment, also utilizing a helical spring 98 in which the body 86 does not have a flange. The upper end of the body 86 is provided with external threads so that the transducer may be threaded into a mounting surface. A seal is accomplished by virtue of the engagement of the pipe threads of the transducer body 86 with the mating threads of the mounting surface (not seen).

The transducer shown in FIG. 6 and 7, and in the cross-sectional view of FIGS. 8 and 9 are illustrative of the fact that the appearance of the transducer which incorporates the principles of this invention may vary considerably without departing from the spirit and scope of this disclosure.

The claims in the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An improved transducer for transmitting and receiving sonic energy for use in measuring the speed of sound characteristics of a fluid medium comprising:

a housing having a cylindrical opening and having a forward end and a rearward end;

a transducer crystal element having a natural frequency of deformation when electrically stimulated;

an acoustic end member sealably closing the forward end of said housing cylindrical opening, the end member having a rearward portion forming a sonic window and a forward portion, the forward portion providing an integral reflector portion spaced from the sonic window portion with means for fluid medium to freely pass between the sonic window portion and the reflector portion;

means in said cylindrical opening rearwardly of said crystal element for applying force against said crystal element to cause intimate contact of said crystal element and said sonic window portion;

a thrust transmitting sphere in the path of said applied force serving to ensure uniform load of force of said crystal element against said window;

said acoustic end member being formed of a base portion which sealably closes the forward end of said housing cylindrical opening, a target portion providing a reflective surface spaced from said base portion, and spaced apart leg portions integrally connecting said base portion and said target portion; and means of providing separate electrical paths for electrical stimulation of said crystal element.

2. An improved transducer according to claim 1 wherein the outer surfaces of said base portion and target portion of said acoustic end member and said housing are confined within an imaginary cylindrical surface.

3. An improved transducer according to claim 1 wherein said housing and integral acoustic end member are formed free of crevices, the transducer being thereby adaptable for use in sanitary applications.

4. An improved transducer according to claim 1 including:

a cylindrical dampening member rearwardly of said crystal element and in contact with said rearward face thereof, said dampening member being in the path of said applied force against said crystal element.

5. An improved transducer according to claim 4 wherein said cylindrical dampening member is in the form of a plurality of thin cylindrical discs.

6. An improved transducer according to claim 5 wherein said cylindrical discs are formed of non-ferrous metal.

7. An improved transducer according to claim 1 including a first and a second cylindrical thrust imparting disc, each disc having a recess in one surface of its cylindrical axis, said discs being positioned within said cylindrical opening between said force applying means and said transducer crystal element with their axes in the path of force applied by said means and said thrust transmitting sphere being positioned between the discs and received in the recesses therein.

8. An improved transducer according to claim 1 including an insulating sleeve within said cylindrical opening surrounding said crystal element and portions of said force applying means having electrical continuity with said crystal element rearward face.

9. An improved transducer according to claim 1 including an electrical contact washer within said cylindrical opening and positioned between said crystal element rearward face and said force applying means, the washer having an opening therethrough and said force applying means having a longitudinal opening therein; and an insulated conductor having one end connected to said electrical contact washer and the other end extending externally of the transducer through said force applying means longitudinal opening.

10. An improved transducer according to claim 1 wherein said housing cylindrical opening is internally threaded in the portion adjacent said rearward end and wherein said force applying means is in the form of an externally threaded compression screw threadably received in said cylindrical opening internally threaded rearward end portion.

11. An improved transducer according to claim 1 wherein said acoustic end member is metallic and is welded in position to said housing.

12. An improved transducer for transmitting and/or receiving sonic energy comprising:

a housing having a cylindrical opening and having a forward end and a rearward end;

a cylindrical transducer crystal element having a forward planar face and an opposed rearward face, the crystal element having a natural frequency of deformation when electrically stimulated;

a sonic window member sealably closing the forward end of said housing cylindrical opening:

means in said cylindrical opening rearwardly of said crystal transducer for applying force against said transducer element rearward face to cause intimate contact of said crystal element forward face and said sonic window rearward face;

spring means between said means of applying force and said crystal element;

a thrust transmitting sphere in the path of said applied force serving to ensure uniform load of force of said crystal element against said window; and means of providing separate electrical paths between said crystal element forward and rearward faces.

13. An improved transducer according to claim 12 wherein said spring means is in the form of a helical spring.

14. An improved transducer according to claim 12 wherein said spring means is in the form of a plurality of Belleville spring washers.

15. An improved transducer according to claim 12 including:

a cylindrical dampening member rearwardly of said crystal element and in contact with said rearward face thereof, said dampening member being in the path of said applied force against said crystal element.

16. An improved transducer according to claim 15 wherein said cylindrical dampening member is in the form of a plurality of thin cylindrical discs.

17. A transducer for high pressure environments according to claim 16 wherein said cylindrical discs are formed of non-ferrous metal.

18. An improved transducer according to claim 12 including a first and a second cylindrical thrust imparting disc, each disc having a recess in one surface of its cylindrical axis, said discs being positioned within said cylindrical opening between said force applying means and said transducer crystal element with their axes in the path of force applied by said means and said thrust transmitting sphere being positioned between the discs and received in the recesses therein.

19. An improved transducer according to claim 12 including an insulating sleeve within said cylindrical opening surrounding said crystal element and portions of said force applying means having electrical continuity with said crystal element rearward face.

20. An improved transducer according to claim 12 including an electrical contact washer within said cylindrical opening and positioned between said crystal element rearward face and said force applying means, the washer having an opening therethrough and said force applying means having a longitudinal opening therein; and an insulated conductor having one end connected to said electrical contact washer and the other end extending externally of the transducer through said force applying means longitudinal opening.

21. An improved transducer according to claim 12 wherein said housing cylindrical opening is internally threaded in the portion adjacent said rearward end and wherein said force applying means is in the form of an externally threaded compression screw threadably received in said cylindrical opening internally threaded rearward end portion.

22. An improved transducer according to claim 12 wherein said acoustic window is metallic and is welded in position in said cylindrical opening.

23. An improved transducer according to claim 12 wherein said sonic window member is in the form of an acoustic end member, the end member having a rearward portion forming said sonic window and a forward portion providing an integral reflection portion spaced from the sonic window portion with means for a fluid medium to freely pass between the sonic window portion and the reflection portion.

24. An improved transducer according to claim 23 wherein said acoustic end member is formed of a base portion which sealably closes the forward end at said housing cylindrical opening, a target portion providing a reflective surface spaced from said base portion, and spaced apart leg portions integrally connecting said base portion and said target portion.

25. An improved transducer according to claim 24 wherein the outer surfaces of said base portion and target portion of said acoustic end member and said housing are confined within an imaginary cylindrical surface

* * * * *